US011883175B2

(12) United States Patent
Ramos Murguialday et al.

(10) Patent No.: US 11,883,175 B2
(45) Date of Patent: Jan. 30, 2024

(54) PARETIC LIMB REHABILITATION METHODS AND SYSTEMS

(71) Applicants: FUNDACION TECNALIA RESEARCH & INNOVATION, Derio (ES); THE REGENTS OF THE UNIVERSITY OF CALIFORNIA, Oakland, CA (US); EBERHARD KARLS UNIVERSITÄT TÜBINGEN, Tübingen (DE)

(72) Inventors: Ander Ramos Murguialday, Donostia (ES); Andrea Sarasola, Tubingen (DE); Jose Miguel Carmena Ramon, Berkeley, CA (US); Joseph McIntyre, Donostia (ES)

(73) Assignee: FUNDACION TECNALIA RESEARCH & INNOVATION, Derio (ES)

(*) Notice: Subject to any disclaimer, the term of this patent is extended or adjusted under 35 U.S.C. 154(b) by 1189 days.

(21) Appl. No.: 16/418,186

(22) Filed: May 21, 2019

(65) Prior Publication Data
US 2019/0269343 A1 Sep. 5, 2019

Related U.S. Application Data

(63) Continuation of application No. PCT/ES2016/070833, filed on Nov. 22, 2016.

(51) Int. Cl.
*A61B 5/24* (2021.01)
*A61B 5/11* (2006.01)
(Continued)

(52) U.S. Cl.
CPC .............. *A61B 5/24* (2021.01); *A61B 5/1107* (2013.01); *A61B 5/1122* (2013.01);
(Continued)

(58) Field of Classification Search
CPC . A61B 2505/09; A61B 5/1107; A61B 5/1122; A61B 5/1124; A61B 5/1128;
(Continued)

(56) References Cited

U.S. PATENT DOCUMENTS

| | | | |
|---|---|---|---|
| 2010/0114329 A1 | 5/2010 | Casler et al. | |
| 2014/0277582 A1* | 9/2014 | Leuthardt | A61B 5/0006 623/25 |
| 2015/0112451 A1 | 4/2015 | Dechev et al. | |

FOREIGN PATENT DOCUMENTS

WO 2016076886 A1 5/2016

OTHER PUBLICATIONS

Blana D, et al. Feasibility of using combined EMGand kinematic signals for prosthesis control: A simulation study using a virtual reality environment. Journal of Electromyography and Kinesiology. Aug. 1, 2016;29:21-7 (Year: 2016).*
(Continued)

*Primary Examiner* — Alex M Valvis
*Assistant Examiner* — Yasmeen S Warsi
(74) *Attorney, Agent, or Firm* — Edell, Shapiro & Finnan, LLC

(57) ABSTRACT

Generator systems and methods are provided for generating a neuromuscular-to-motion decoder from a healthy limb. The generator system is configured to receive neuromuscular signals from neuromuscular sensors associated to predefined muscle/nerve locations of at least one pair of agonist and antagonist muscles/nerves of the healthy limb, obtained during performance by the person of a predefined exercise (defined by predefined exercise data) with the healthy limb; to receive motion signals from motion sensors associated to predefined positions of the healthy limb, during performance by the person of the predefined exercise with the healthy limb; and to generate the neuromuscular-to-motion decoder by mapping the neuromuscular signals to the motion signals
(Continued)

over time using a mapping method. Rehabilitation systems are also provided for rehabilitating a paretic limb by using a neuromuscular-to-motion decoder produced by a generator system.

16 Claims, 7 Drawing Sheets

(51) Int. Cl.
    *A61B 5/22*     (2006.01)
    *A61B 5/00*     (2006.01)
    *A61H 1/02*     (2006.01)
    *A61F 2/54*     (2006.01)
    *A61F 2/58*     (2006.01)
    *A61F 2/72*     (2006.01)
    *A61B 5/389*     (2021.01)
    *A61F 2/68*     (2006.01)
    *A61F 2/70*     (2006.01)

(52) U.S. Cl.
CPC ............ *A61B 5/1124* (2013.01); *A61B 5/224* (2013.01); *A61B 5/389* (2021.01); *A61B 5/6824* (2013.01); *A61F 2/54* (2013.01); *A61F 2/583* (2013.01); *A61F 2/72* (2013.01); *A61H 1/0237* (2013.01); *A61H 1/0274* (2013.01); *A61B 5/1128* (2013.01); *A61B 5/225* (2013.01); *A61B 5/4052* (2013.01); *A61B 5/4082* (2013.01); *A61B 5/6825* (2013.01); *A61B 5/6826* (2013.01); *A61B 2505/09* (2013.01); *A61F 2/70* (2013.01); *A61F 2002/543* (2013.01); *A61F 2002/6872* (2013.01); *A61H 2201/501* (2013.01); *A61H 2205/06* (2013.01); *A61H 2205/065* (2013.01); *A61H 2205/067* (2013.01); *A61H 2205/10* (2013.01); *A61H 2230/08* (2013.01); *A61H 2230/085* (2013.01); *A61H 2230/60* (2013.01)

(58) Field of Classification Search
CPC ........... A61B 5/224; A61B 5/225; A61B 5/24; A61B 5/389; A61B 5/4052; A61B 5/4082; A61B 5/6824; A61B 5/6825; A61B 5/6826; A61F 2/54; A61F 2/583; A61F 2/70; A61F 2/72; A61F 2002/543; A61F 2002/6872; A61H 1/0237; A61H 1/0274; A61H 2201/501; A61H 2205/06; A61H 2205/065; A61H 2205/067; A61H 2205/10; A61H 2230/08; A61H 2230/085; A61H 2230/60

See application file for complete search history.

(56) References Cited

OTHER PUBLICATIONS

Cesqui, B., Tropea, P., Micera, S. et al. EMG-based pattern recognition approach in post stroke robot-aided rehabilitation: a feasibility study. J NeuroEngineering Rehabil 10, 75 (2013). https://doi.org/10.1186/1743-0003-10-75 (Year: 2013).*
Ramos-Murguialday A, Garcia-Cossio E, Walter A, Cho W, Broetz D, Bogdan M, Cohen LG, Birbaumer N. Decoding upper limb residual muscle activity in severe chronic stroke. Annals of clinical and translational neurology. Jan. 2015;2(1):1-1. (Year: 2015).*
M. Mulas, M. Folgheraiterand G. Gini, "An EMG-controlled exoskeleton for hand rehabilitation," 9th International Conference on Rehabilitation Robotics, 2005. ICORR 2005., 2005, pp. 371-374, doi: 10.1109/ICORR.2005.1501122. (Year: 2005).*
Marchal-Crespo, Laura, and David J. Reinkensmeyer. "Review of control strategies for robotic movement training after neurologic injury." Journal of neuroengineering and rehabilitation 6.1 (2009): 1-15. (Year: 2009).*
Mulas et al., An EMG-controlled Exoskeleton for Hand Rehabilitation, Proceedings of the 2005 IEEE, 9th International Conference on Rehabilitation Robotics, Jun. 28-Jul. 1, 2005, Chicago, IL, USA, pp. 371-374.
International Search Report and Written Opinion in corresponding PCT Application No. PCT/ES2016/070833, dated Jul. 26, 2017, 19 pages.
Blana, "Feasibility of using combined EMG and kinematic signals for prosthesis control: A simulation study using a virtual reality environment", Journal of electromyography and Kinesiology, vol. 29, Jul. 9, 2015, pp. 21-27.
EP Communication, Application No. 16 831 818.6-1113, dated Jul. 20, 2023, 7 pages.

* cited by examiner

PARETIC LIMB REHABILITATION METHODS AND SYSTEMS

CROSS-REFERENCE TO RELATED APPLICATIONS

This application relates to and claims the benefit and priority to International Application No. PCT/ES2016/070833, filed Nov. 22, 2016.

FIELD

The present disclosure relates to methods, systems and computer programs for rehabilitating a paretic limb of a patient.

BACKGROUND

Brain vascular accidents caused by stroke, brain injury, or cerebral paralysis are one of the main causes of long-term motor disability worldwide and in more than 85% of these cases functional deficits in motor control occur. Incidence of first stroke in Europe is about 1.1 million and prevalence about 6 million. Of all stroke survivors showing no active upper limb motion at hospital admission 14% showed complete recovery, 30% showed partial recovery and 56% show little or no recovery, and the grand majority retained sensory function.

Electromyography (EMG) is an electro-diagnostic medicine technique for evaluating and recording the electrical activity produced by skeletal muscles. An EMG signal represents the electric potential generated by muscle cells when these cells are electrically or neurologically activated. The EMG signals are generally used to detect medical abnormalities, activation level, or recruitment order, or to analyse the biomechanics of human or animal movement.

Systems and methods for rehabilitating a paretic limb are known in the state of the art, which are based on using EMG signals from the paretic limb and applying an assistive motion/force through a robot-aided tool.

Some of said systems/methods use EMG signals of the paretic limb as an indicator of the overall generated effort, and trigger a pre-programmed assistive movement when the amplitude of the muscle activation goes over a predefined threshold.

Other known EMG-based systems and methods comprise implemented proportional controllers in which the amount of the provided assistive force is proportional to the amplitude of the EMG signal recorded from the impaired limb.

In some other known EMG-based systems and methods, the direction and amplitude of the intended movement are deduced depending on the EMG signals (from the paretic limb) themselves.

WO2016076886 (A1) discloses a system for motor rehabilitation of a paretic limb of a patient comprising: a first plurality of sensors for registering brain neuro-signals of the patient; a body-actuator couplable to, at least, the paretic limb; a hybrid brain machine interface for decoding brain neurosignals into movements of the body-actuator. The system further comprises: a second plurality of EMG sensors couplable to the paretic limb for registering its neuromuscular activity; means for providing the patient with instructions relative to a series of exercises and/or tasks to be carried out with the paretic limb; and in that upon carrying out a series of training sessions, each session comprising at least a set of such instructions. The hybrid brain machine interface is configured to switch between controlling the movements of the body-actuator based on the decoded brain neurosignals and a hybrid control of the movements of the body-actuator, when a significant level of decodable neuromuscular activity has been registered, the hybrid control being an EMG-gated brain control. The invention also relates to a method for motor rehabilitation of the paretic limb.

SUMMARY

In a first aspect, a generator system is provided for generating a neuromuscular-to-motion decoder from a healthy limb of a person. The generator system comprises neuromuscular sensors, motion sensors, and a controller system.

The controller system (of the generator system) is configured to receive neuromuscular signals obtained by the neuromuscular sensors associated to predefined muscle and/or nerve locations of at least one pair of agonist and antagonist muscles/nerves of the healthy limb. The neuromuscular signals are obtained during performance by the person of a predefined exercise with the healthy limb. The predefined exercise is defined by predefined exercise data.

The controller system (of the generator system) is further configured to receive motion signals obtained by the motion sensors associated to predefined positions of the healthy limb. The motion signals are obtained during performance by the person of the predefined exercise with the healthy limb. The predefined positions of the healthy limb may be such that motions resulting from neuromuscular activity (represented by the obtained neuromuscular signals) are suitably sensed by the motion sensors.

The controller system (of the generator system) is still further configured to generate the neuromuscular-to-motion decoder by mapping the neuromuscular signals to the motion signals over time using a mapping method.

The proposed generator system may be very useful in the sense that the neuromuscular-to-motion decoder produced by the generator system may be used for effectively rehabilitating a paretic limb of a patient.

The neuromuscular-to-motion decoder may be a mathematical function or module defining a mapping or cause-effect relationship between both types of signals, i.e. an evolution over time of motion signals (effect) depending on neuromuscular signals (cause).

In an example, the neuromuscular-to-motion decoder may be generated in the form of a mathematical function by using a statistical method such as e.g. a regression method. In another example, the neuromuscular-to-motion decoder may be a mathematical module implementing e.g. an artificial neural network or the like. The mathematical function or module implementing the neuromuscular-to-motion decoder may be trained based on a machine learning method using the neuromuscular and motion signals from the healthy limb.

The neuromuscular-to-motion decoder may be used as a model representing which motion is derived from which neuromuscular activity in the healthy limb. The neuromuscular-to-motion decoder may thus be used for rehabilitating a paretic limb of a patient by taking the neuromuscular-to-motion decoder as a neuromuscular behaviour of reference to be finally achieved by the paretic limb.

The generator system may be used to generate an initial version of the neuromuscular-to-motion decoder from a healthy limb of a person, and said initial version may be subsequently enriched by using the generator system applied to a healthy limb of other people. Hence, the proposed generator system may be properly used to obtain a powerful neuromuscular-to-motion decoder from several healthy limbs, one of which belonging to a patient to be rehabilitated or not.

In a second aspect, a rehabilitation system is provided for rehabilitating a paretic limb of a patient by using a neuromuscular-to-motion decoder generated by a generator system as the one described before. The rehabilitation system comprises neuromuscular sensors, motion sensors, and a controller system. The paretic limb may be of a same type as a healthy limb taken into account in the generation of the neuromuscular-to-motion decoder.

The controller system (of the rehabilitation system) is configured to receive neuromuscular signals obtained by the neuromuscular sensors associated to predefined muscle and/or nerve locations of the paretic limb corresponding to predefined muscle and/or nerve locations of one (or more) healthy limb(s) taken into account in the generation of the neuromuscular-to-motion decoder. The neuromuscular signals are obtained during an attempt by the patient to perform with the paretic limb a predefined exercise defined by predefined exercise data taken into account in the generation of the neuromuscular-to-motion decoder.

The controller system (of the rehabilitation system) is further configured to input the neuromuscular signals to the neuromuscular-to-motion decoder for causing the neuromuscular-to-motion decoder to output first motion commands. That is, the cause-effect relationship between neuromuscular signals and motion signals from one (or more) healthy limbs is used to infer a motion to be performed by the paretic limb.

The controller system (of the rehabilitation system) is still further configured to receive motion signals obtained by the motion sensors associated to predefined positions of the paretic limb corresponding to predefined positions of the healthy limb taken into account in the generation of the neuromuscular-to-motion decoder. The motion signals are obtained during the attempt by the patient to perform the predefined exercise with the paretic limb.

The controller system (of the rehabilitation system) is additionally configured to determine trajectory data defining a trajectory to be followed by the paretic limb depending on a deviation between the motion signals and the predefined exercise data, and to determine second motion commands depending on the determined trajectory data to be followed by the paretic limb.

The controller system (of the rehabilitation system) is still additionally configured to determine final motion commands depending on the first motion commands and the second motion commands, and to send the final motion commands to a body actuator associated to the paretic limb for controlling the body actuator so as to stimulate (or induce) the patient to perform the predefined exercise with the paretic limb.

The proposed rehabilitation system permits inducing a "hybrid" motion of the paretic limb combining a motion component due to neuromuscular activity detected in the paretic limb (first motions commands), and another motion component aimed at guiding the paretic limb towards a valid trajectory according to the predefined exercise data (second motion commands).

Once the patient has achieved a high level of rehabilitation, the guiding component (second motion commands) may be highly reduced for causing the neuromuscular activity of the paretic limb (first motion commands) to be the main driving inducer of the motion of the paretic limb.

During initial and intermediate (i.e. non-final) rehabilitation stages, the first motion commands may represent an incorrect motion of the paretic limb and the second motion commands may represent a correction of said incorrect motion aimed at redirecting the limb towards a valid trajectory according to the predefined exercise data.

This hybrid motion may cause a visual and/or proprioceptive feedback on the patient when guiding the patient to finally complete the exercise. This feedback may provide the patient with information about the correctness of his/her muscular activations and hence, may establish a closed-loop system that might lead to the activation of neuro-plastic mechanisms that can restore the motor function. Other types of feedback that can be provided are e.g. haptic, auditory, etc.

The generator and rehabilitation systems proposed herein permit predicting kinematic (or motion) signals from the neuromuscular activity of the paretic limb and, therefore, establishing a continuous myoelectric control of the body actuator (e.g. an exoskeleton).

In some examples, a body actuator other than an exoskeleton may be used, in which case additional decoding(s) may be needed. For example if a Functional electrical stimulation (FES) system is used, the motion signals may be mapped into electrostimulation signals that may cause motions of the paretic limb according to the motion signals.

An exoskeleton and a FES system may cooperate to function as body actuator. Other neuromuscular stimulation systems based on e.g. ultrasound waves and/or optical (e.g. infrared) waves may also be used as body actuator, in cooperation or not with an exoskeleton and/or a FES system.

The person taken into account by the generator system to generate the neuromuscular-to-motion decoder and the patient rehabilitated by the rehabilitation system may coincide or not. In the first case, a mirrored effect may be achieved in the sense that the neuromuscular behaviour of the healthy limb of the patient may be someway replicated on the paretic limb of the patient using the rehabilitation system. In the second case, a neuromuscular-to-motion decoder generated from one or more healthy limbs of people different from the patient may be used to rehabilitate the patient through the rehabilitation system also with acceptable results.

When the person "processed" by the generator system coincides with the patient "processed" by the rehabilitation system, the use of neuromuscular and kinematic/motion signals from the healthy limb to generate the neuromuscular-to-motion decoder enables the creation of a subject-specific model of correct activity.

The participation of agonist-antagonist muscle/nerve pairs permits suitably controlling the compensatory over-activation of antagonist muscles/nerves inherent in stroke patients.

Providing intuitive feedback based on a model of healthy activity could inhibit pathological synergies and enhance the re-integration of the correct and natural patterns of muscle/nerve activations.

The suggested rehabilitation system has been proven to be applicable not only to mild and moderate but also to severely paralysed patients, who often retain some residual neuromuscular activity in spite of being unable to produce any movement of the affected limb. Hence, patients who are not eligible for many prior art rehabilitation methods (and systems) may benefit from the proposed rehabilitation system.

This proposed neuromuscular-powered (rehabilitation) system may require continuous activation of the paretic muscles/nerves to drive the movement of the body actuator, thereby guaranteeing the engagement of the patient at all times during the rehabilitation therapy.

Given final motion commands causing an actuation of the body actuator and given neuromuscular signals from which said final motion commands are derived, less than 300 ms may elapse between the actuation of the body actuator and the obtaining of the neuromuscular signals. Such a contingent link between action and feedback may effectively promote plasticity and, hence, learning and rehabilitation in the patient.

The proposed generator and rehabilitation systems may thus permit an effective rehabilitation without the need of processing brain neuro-signals, as it is required in the case of some prior art systems. Hence, the suggested generator and rehabilitation systems may be significantly simpler and cheaper than prior art systems based on processing brain neuro-signals.

In some examples of the generator system and/or the rehabilitation system, the neuromuscular sensors may comprise one or more electromyography (EMG) sensors, and/or one or more electroneurography (ENG) sensors, and/or one or more ultrasound sensors, and/or one or more optical sensors. Said sensors may be invasive or not.

ENG sensors generate ENG signals representing measurements of the electrical activity of a nerve, ultrasound sensors measure mechanical properties of a muscle/nerve based on ultrasound waves, and optical sensors measure optical properties of a muscle/nerve based on optical waves (e.g. infrared waves).

The generator system and/or the rehabilitation system may be constituted by means which may be electronic means or computing means used interchangeably. That is, a part of the means may be electronic means and the other part may be computer means, or all the means may be electronic means (fully electronic system) or all the means may be computer means (fully computing system).

Examples of systems comprising only electronic means may be a CPLD (Complex Programmable Logic Device), an FPGA (Field Programmable Gate Array) or an ASIC (Application-Specific Integrated Circuit).

More detailed descriptions of the generator and rehabilitation systems and optional features thereof are disclosed in other parts of the description.

In a third aspect, a generator method is provided for generating a neuromuscular-to-motion decoder from a healthy limb of a person. The generator method comprises receiving neuromuscular signals obtained by neuromuscular sensors associated to predefined muscle and/or nerve locations of at least one pair of agonist and antagonist muscles/nerves of the healthy limb. The neuromuscular signals are obtained during performance by the person of a predefined exercise with the healthy limb. The predefined exercise is defined by predefined exercise data.

The generator method further comprises receiving motion signals obtained by motion sensors associated to predefined positions of the healthy limb. The motion signals are obtained during performance by the person of the predefined exercise with the healthy limb.

The generator method still further comprises generating the neuromuscular-to-motion decoder by mapping the neuromuscular signals to the motion signals over time using a mapping method. The neuromuscular-to-motion decoder may be used for rehabilitating a paretic limb.

Since the proposed generator method is suitable for being performed by the generator system, all the aspects and principles commented with respect to the generator system can be similarly attributed to the generator method.

In a fourth aspect, a rehabilitation method is provided for rehabilitating a paretic limb of a patient by using a neuromuscular-to-motion decoder generated by a generator method as the one previously described.

The rehabilitation method comprises receiving neuromuscular signals obtained by neuromuscular sensors associated to predefined muscle and/or nerve locations of the paretic limb corresponding to predefined muscle and/or nerve locations of a healthy limb taken into account in the generation of the neuromuscular-to-motion decoder. The neuromuscular signals are obtained during an attempt by the patient to perform with the paretic limb a predefined exercise defined by predefined exercise data taken into account in the generation of the neuromuscular-to-motion decoder.

The rehabilitation method further comprises inputting the neuromuscular signals to the neuromuscular-to-motion decoder for causing the neuromuscular-to-motion decoder to output first motion commands.

The rehabilitation method still further comprises receiving motion signals obtained by motion sensors associated to predefined positions of the paretic limb corresponding to predefined positions of the healthy limb taken into account in the generation of the neuromuscular-to-motion decoder. The motion signals are obtained during the attempt by the patient to perform the predefined exercise with the paretic limb.

The rehabilitation method additionally comprises determining trajectory data defining a trajectory to be followed by the paretic limb depending on a deviation between the motion signals and the predefined exercise data, and determining second motion commands depending on the determined trajectory data to be followed by the paretic limb.

The rehabilitation method still additionally comprises determining final motion commands depending on the first motion commands and the second motion commands, and sending the final motion commands to a body actuator associated to the paretic limb for controlling the body actuator so as to stimulate (or induce) the patient to perform the predefined exercise with the paretic limb.

Since the proposed rehabilitation method is suitable for being performed by the rehabilitation system, all the aspects and principles commented with respect to the rehabilitation system can be similarly attributed to the rehabilitation method.

In a fifth aspect, a computing system is provided comprising a memory and a processor, embodying instructions stored in the memory and executable by the processor, the instructions comprising functionality to execute a generator method for generating a neuromuscular-to-motion decoder from a healthy limb of a person.

This computing system may be a part of the generator system, i.e. a computing system inside the generator system, or may be the generator system itself.

In a sixth aspect, a further computing system is provided comprising a memory and a processor, embodying instructions stored in the memory and executable by the processor, the instructions comprising functionality to execute a rehabilitation method for rehabilitating a paretic limb of a patient.

This further computing system may be a part of the rehabilitation system, i.e. a computing system inside the rehabilitation system, or may be the rehabilitation system itself.

In a seventh aspect, a computer program product is provided comprising program instructions for causing a computing system to perform a generator method for generating a neuromuscular-to-motion decoder from a healthy limb of a person.

The computing system executing these program instructions may be a part of the generator system (i.e. a sub-system inside the generator system configured to reproduce the generator method described above) or may be the generator system itself.

In an eighth aspect, a further computer program product is provided comprising program instructions for causing a computing system to perform a rehabilitation method for rehabilitating a paretic limb of a patient.

The computing system executing these program instructions may be a part of the rehabilitation system (i.e. a sub-system inside the rehabilitation system configured to reproduce the rehabilitation method described above) or may be the rehabilitation system itself.

Any of the aforementioned computer program products may be embodied on a storage medium (for example, a CD-ROM, a DVD, a USB drive, on a computer memory or on a read-only memory) or carried on a carrier signal (for example, on an electrical or optical carrier signal).

Any of said computer programs may be in the form of source code, object code, a code intermediate source and object code such as in partially compiled form, or in any other form suitable for use in the implementation of the corresponding method. The carrier may be any entity or device capable of carrying the computer program.

For example, the carrier may comprise a storage medium, such as a ROM, for example a CD ROM or a semiconductor ROM, or a magnetic recording medium, for example a hard disk. Further, the carrier may be a transmissible carrier such as an electrical or optical signal, which may be conveyed via electrical or optical cable or by radio or other means.

When any of the computer programs is embodied in a signal that may be conveyed directly by a cable or other device or means, the carrier may be constituted by such cable or other device or means.

Alternatively, the carrier may be an integrated circuit in which the computer program is embedded, the integrated circuit being adapted for performing, or for use in the performance of, the relevant methods.

These and other advantages and features will become apparent in view of the detailed description and drawings.

BRIEF DESCRIPTION OF THE DRAWINGS

Non-limiting examples of the present disclosure will be described in the following, with reference to the appended drawings, in which.

DETAILED DESCRIPTION

Figure 1:
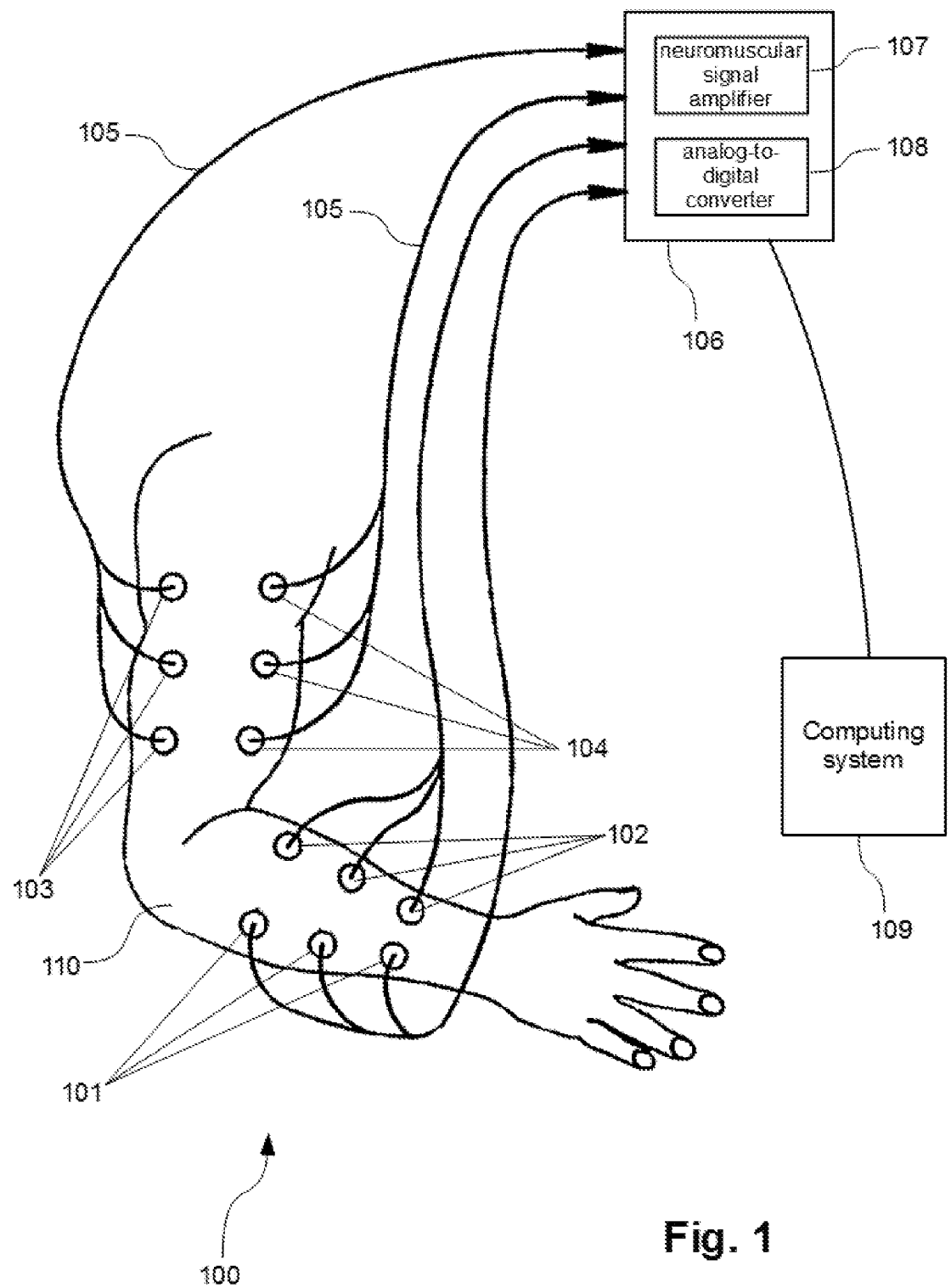
FIG. 1 is a schematic representation of a generator system according to examples.
Figure 2:
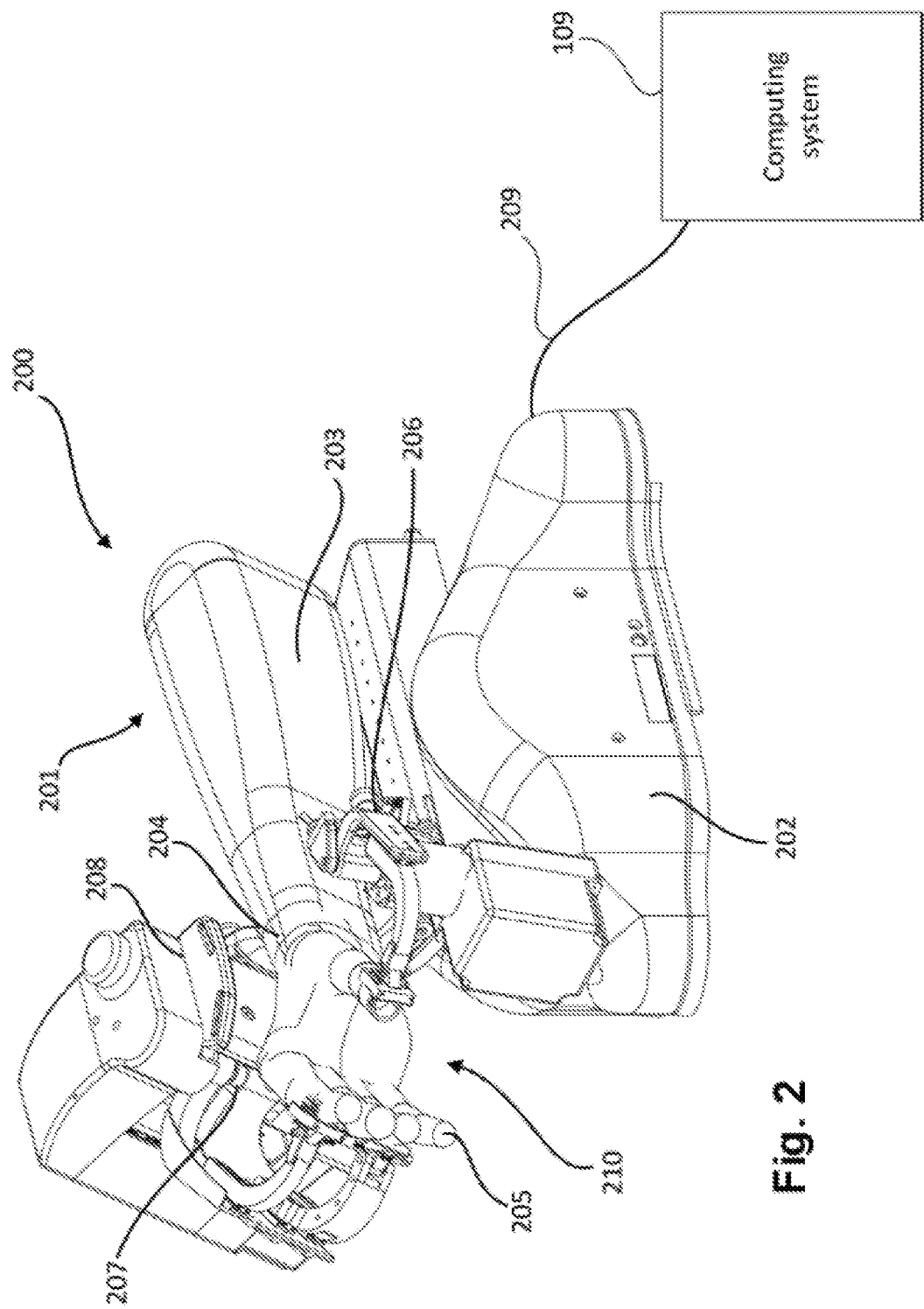
FIG. 2 is a schematic representation of a rehabilitation system according to examples.

An example of generator system is schematically shown in FIG. 1, and an example of rehabilitation system is schematically shown in FIG. 2. The generator system may be comprised in the rehabilitation system or not.

The generator system 100 may be configured to be applied to a healthy arm 110 but, in other examples, the system 100 could be configured to be applied to a healthy leg.

The generator system 100 may comprise a plurality of neuromuscular sensors 101-104, a control unit 106 and corresponding connections 105 connecting the neuromuscular sensors 101-104 and the control unit 106. In the particular case shown, the connections 105 are wired connections. However, all or part of said connections may be wireless. The generator system 100 may further comprise a computing (or controller) system 109.

The neuromuscular sensors 101-104 may comprise EMG sensor(s) and/or ENG sensor(s) and/or ultrasound sensor(s) and/or optical sensor(s) aimed at the same purpose. The neuromuscular sensors 101-104 may be invasive or not.

The control unit 106 may comprise a neuromuscular signal amplifier 107 for amplifying analogic neuromuscular signals from the neuromuscular sensors 101-104, and an Analog-to-Digital (AD) converter 108 for converting the amplified neuromuscular signals into digital neuromuscular signals.

A first set of neuromuscular sensors 101, 102 may be configured to be applied to a first pair of agonist and antagonist muscles/nerves of the arm (or leg) 110. A second set of neuromuscular sensors 103, 104 may be configured to be applied to a second pair of agonist and antagonist muscles/nerves of the arm (or leg) 110. Other sensor configurations different from the one shown are also possible. For example, the number of sensors applied to an agonist and to its antagonist may not coincide, i.e. unbalanced numbers of sensors are also possible.

The sensors (e.g. electrodes) 101-104 may be, for example, bipolar surface electrodes with conductive gel, and may be provided (or not) as an array with a high density of electrodes. The sensors (e.g. electrodes) 101-104 may be configured to be adhered (or, in some examples, implanted) to the skin of the patient for sensing neuromuscular activity at corresponding muscle and/or nerve locations. The sensors 101-104 may comprise e.g. subcutaneous sensors (e.g. electrodes).

The generator system may further comprise motion sensors (not shown) including e.g. inertial, magnetic or optical sensors (such as e.g. accelerometers, gyroscopes, etc.) arranged and configured to provide functionalities of motion detection and quantification. These sensors may be included (or embedded) in suitable devices, such as e.g. data gloves or the like, or even in an exoskeleton movable by the healthy limb with or without guiding functionalities aimed at guiding the healthy limb to perform a predefined exercise.

The control unit 106 may be connected to the computing system 109 in such a way that the computer 109 may receive neuromuscular signals from the sensors 101-104 during performance of a predefined exercise. Suitable connections between the motion sensors and the computing system 109 may also exist for the computer 109 to receive motion signals generated by the motion sensors.

The computing system 109 may comprise a memory and a processor. The memory may store a computer program comprising instructions that are executable by the processor for causing the performance of a generator method for generating a neuromuscular-to-motion decoder from a healthy limb. This "generator" computer program may be a standalone program or may require the loading of external module(s) or other pieces of software.

A resulting neuromuscular-to-motion decoder may be stored in a repository (e.g. hard disk) associated to the computing system 109. This repository may be local or remote with respect to the computer system 109.

FIG. 2 is a schematic representation of a rehabilitation system for rehabilitating a paretic limb, according to examples. The rehabilitation system may comprise a configuration similar to the one shown in FIG. 1, with neuromuscular sensors for obtaining signals representing the neuromuscular activity of the paretic limb during performance of a predefined exercise. This predefined exercise may be the same as the one taken into account for obtaining the neuromuscular-to-motion decoder to be used for rehabilitating the paretic limb. The rehabilitation system may further comprise corresponding motions sensors and a computing (or controller) system 109.

In some examples, a generator system such as the one shown in FIG. 1 may be comprised in a rehabilitation system such as the one shown in FIG. 2. In this case, the neuromuscular sensors used to generate the neuromuscular-to-motion decoder may be reused to obtain neuromuscular signals from a paretic limb to be rehabilitated. The same computing system 109 may be employed for e.g. executing both a generator method and a rehabilitation method as explained in other parts of the description.

In the particular case of FIG. 2, it is shown a robotic exoskeleton 200 (as body actuator) configured to be applied to an arm 201. However, in other examples, the robotic exoskeleton 200 may be mountable to a leg. In other examples, the body actuator may be a Functional electrical stimulation (FES) system, or any other type of system that could provide the patient with feedback about his/her neuromuscular activity. In further examples, an exoskeleton and a FES system may cooperate to function as a hybrid body actuator or the like. Neuromuscular stimulation systems based on ultrasound waves and/or optical waves may also be used, in combination or not with an exoskeleton and/or a FES system for body actuation.

The robotic exoskeleton 200 may be movable according to a number of degrees of freedom so as to permit the motion of different segments of the arm 201, such as e.g. upper arm (not shown), forearm 203, wrist 204 and fingers 205. The exoskeleton 200 may be configured to permit functional movements of the arm (or leg).

In particular examples, the robotic exoskeleton 200 may comprise a mobile base 202 and a hand-module 210 that may be mountable on the mobile base 202.

The mobile base 202 may have, in some examples, three degrees of freedom and may (optionally) include a camera for tracking bi-dimensional movements of the base on a plane of reference. Other quantities of degrees of freedom different from three may be considered in other examples.

The hand-module 210 may have, in some examples, four degrees of freedom and (optionally) may be configured to track the motion of the wrist 204 and/or fingers 205. Other numbers of degrees of freedom may be considered in different examples.

The robotic exoskeleton 200 may comprise motors 206-208 each configured to cause movement of the exoskeleton in a corresponding degree of freedom.

For the sake of simplicity, only some motors 206-208 are indicated in the figure. The exoskeleton 200 may however comprise other quantities of motors, depending on e.g. the number of degrees of freedom under consideration.

A controller of the motors 206-208 of the exoskeleton 200 may be connectable to the computer system 109 through a connection 209 that may be e.g. a USB connection. Other types of connections are also possible, such as e.g. wireless connections.

Different motors 206-208 of the exoskeleton 200 may communicate between them through a CAN communication, so that a proper communication channel between the computer system 109 and the motors 206-208 may be defined.

The exoskeleton 200 may also provide functionalities of motion detection and quantification. These functionalities may be provided through e.g. rotary encoders (a type of motion sensors) configured to generate motion signals representing motion conditions associated to different degrees of freedom. A (rotatory) encoder may be included in a corresponding motor 206-208.

Motion sensors similar to the ones described with reference to generator system (of FIG. 1) may also be comprised in rehabilitation system (of FIG. 2). In the case that the generator system is comprised in the rehabilitation system, the motion sensors of the generator system may be reused to participate in rehabilitating a paretic limb.

In any case, with respect to motion sensors of either a generator or rehabilitation system or a combination thereof, a motion condition (sensed by a motion sensor) may comprise e.g. at least one of a position, a velocity, an acceleration, a torque, a force etc. in a given degree of freedom.

Additionally or alternatively to the encoders described before, known inertial, magnetic or optical sensors embedded in suitable devices, such as e.g. data gloves, or in wearable parts of the exoskeleton, may be used to implement the functionalities of motion detection and quantification.

The communication channel(s) established between the computer system 109 and the motors 206-208 of the exoskeleton 200 may permit the computer system 109 to receive the motion signals (from encoders). As explained in detail in other parts of the description, said motion signals may be suitably processed by the computer system 109 in the context of methods for rehabilitating a paretic limb.

The communication channel(s) between the computer system 109 and the motors 206-208 of the exoskeleton 200 may permit the computer system 109 to generate and send (final) motion commands to the exoskeleton 200. These (final) motion commands may induce the exoskeleton 200 to move as required in the context of methods for rehabilitating a paretic limb. Details about this are disclosed in other parts of the description.

The camera included in the mobile base 202 may also be connectable to the computer system 109 through e.g. a USB or wireless connection and/or may optionally permit determining bi-dimensional positions of the base 202 on the plane of reference. Said positions may be determined, for example, by decoding Data-matrix codes printed on a table defining the plane of reference.

The exoskeleton 200 may be configured to be indistinctly applied to a (right or left) healthy arm/leg, and to a (right or left) paretic arm/leg. This way, the same exoskeleton 200 may be used for performing both a generator method (with healthy limb or limbs) and a rehabilitation method (with paretic limb). Details about how the exoskeleton may be used in said generator and rehabilitation methods are explained in detail in other parts of the description.

Alternatively to an exoskeleton, such as the one of FIG. 2, the rehabilitation system may comprise another type of body actuator, such as e.g. a neuromuscular stimulation system or a combination thereof. Examples of neuromuscular stimulation systems are e.g. a Functional electrical stimulation (FES) system, a neuromuscular stimulation system based on ultrasound waves, a neuromuscular stimulation system based on optical waves, etc.

The neuromuscular stimulation system (e.g. FES system) may be configured to provide functionalities of motion induction substantially equivalent to those provided by the exoskeleton as described before. That is, based on received motion commands, the (FES) system may (electro-) stimulate the arm (or leg) 201 in such a way that required motions of the arm (or leg) 201 are induced with same or similar results as if the exoskeleton were used.

Permitted motion directions substantially equivalent to the degrees of freedom described in relation to the exoskeleton may be taken into account if a neuromuscular stimulation system (e.g. FES system) is used as body actuator. That is, in the case of using a FES system instead of an exoskeleton, the arm 201 may be electro stimulated so as to cause the motion of the arm 201 only in said permitted motion directions.

The memory of the computing system 109 may further store a computer program comprising instructions that are executable by the processor for performing a rehabilitation method for rehabilitating a paretic limb. This "rehabilitation" program may be a separate program with respect to the "generator" program described in relation to FIG. 1, or not. In this last case, the "rehabilitation" program and the "generator" program may be different sub-programs (or sub-modules) of a same computer program providing both types of (generator and rehabilitation) functionalities.

The neuromuscular-to-motion decoder to be used by the rehabilitation system may be retrieved from a repository (e.g. hard disk) associated to the computing system 109. This repository may be local or remote with respect to the computer system 109.

Figure 3:
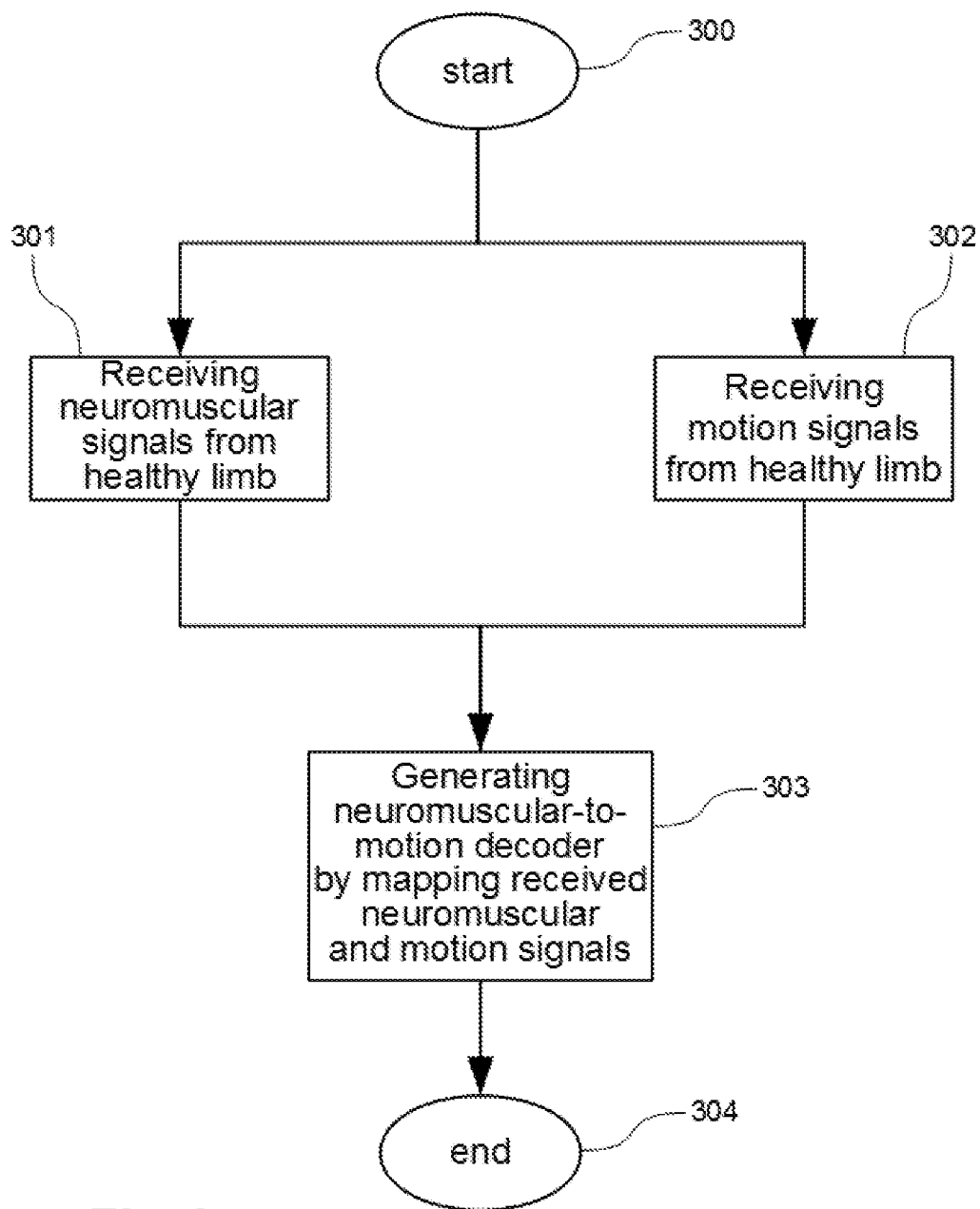
FIG. 3 is a flow chart schematically illustrating a generator method according to examples.

FIG. 3 shows a flowchart schematically illustrating an example of a generator method for generating a neuromuscular-to-motion decoder from a healthy limb. This generator method may take into account (neuromuscular and motion) signals from a healthy arm of a person during performance of a predefined exercise by the person with the healthy arm.

This generator method may be performed by using a generator system equal or similar to the ones described before with reference to previous figures. References to said previous figures may be thus included along the following description about FIG. 3.

At block 300, the method may be started as a result of receiving a starting condition, such as e.g. a user request inputted by an operator of the generator system.

At this point, the person may be requested to perform the predefined exercise with the healthy arm. The predefined exercise may be defined by predefined exercise data which is available to the computer system 109.

In some examples, the computer system 109 may process the predefined exercise data to generate reproducible data and send it to a reproducing system, so as to provide audio and/or visual instructions to the person of how to perform the predefined exercise.

At block 301, neuromuscular signals may be received (by the computer system 109) from neuromuscular sensors 101-104 attached to the healthy arm, during performance of the predefined exercise.

The neuromuscular sensors 101-104 may be attached to regions of the healthy arm associated to predefined muscle and/or nerve locations of at least one pair of agonist and antagonist muscles/nerves of the healthy arm. The attachment of the neuromuscular sensors 101-104 may be equal or similar to the attachment shown in FIG. 1, for example.

At block 302, motion signals may be received from motion sensors associated to predefined positions of the healthy limb, during performance of the predefined exercise. The nature of said motion sensors and corresponding motion signals are explained in detail in other parts of the description, in any case wherein an exoskeleton or a stimulation system (e.g. FES system) or a combination thereof is employed.

At block 303, a neuromuscular-to-motion decoder may be generated for each of all or some of the degrees of freedom (in exoskeleton-based examples) or permitted motion directions (in examples based on a stimulation system) under consideration.

Given a particular degree of freedom (or permitted motion direction), a neuromuscular-to-motion decoder may be generated by mapping the received neuromuscular signals and motion signals corresponding to said degree of freedom (or permitted motion direction). It is also possible to generate a single neuromuscular-to-motion decoder with different outputs corresponding to different degrees of freedom.

A neuromuscular-to-motion decoder may be, for example, a mathematical function or module defining a cause-effect relationship between both types of signals, i.e. an evolution over time of motion signals (effect) depending on neuromuscular signals (cause).

A diversity of mapping methods may be used to generate the neuromuscular-to-motion decoder, such as e.g. machine learning methods, statistical methods, datamining methods, etc. or a combination of at least some of them. In particular, linear regression, non-linear regression, Lasso regression, ridge regression, Kalman filter, support vector machine, neural network, fuzzy logic, etc. may be employed for that purpose.

For instance, a mathematical module may result from e.g. training a machine learning model based on the received neuromuscular signals and motion signals. A mathematical module may therefore result from said training that is configured to output motion values corresponding to input neuromuscular values.

In other examples, the received neuromuscular and motion signals (for different degrees of freedom or permitted motion directions under consideration) may be correlated (mapped), so that a shape or profile of a "cloud" of points corresponding to the neuromuscular and motion signals over time is modelled. A function may result from said correlation that is configured to output motion values corresponding to input neuromuscular values according to said modelling of the cloud of neuromuscular-motion points.

Figure 4:
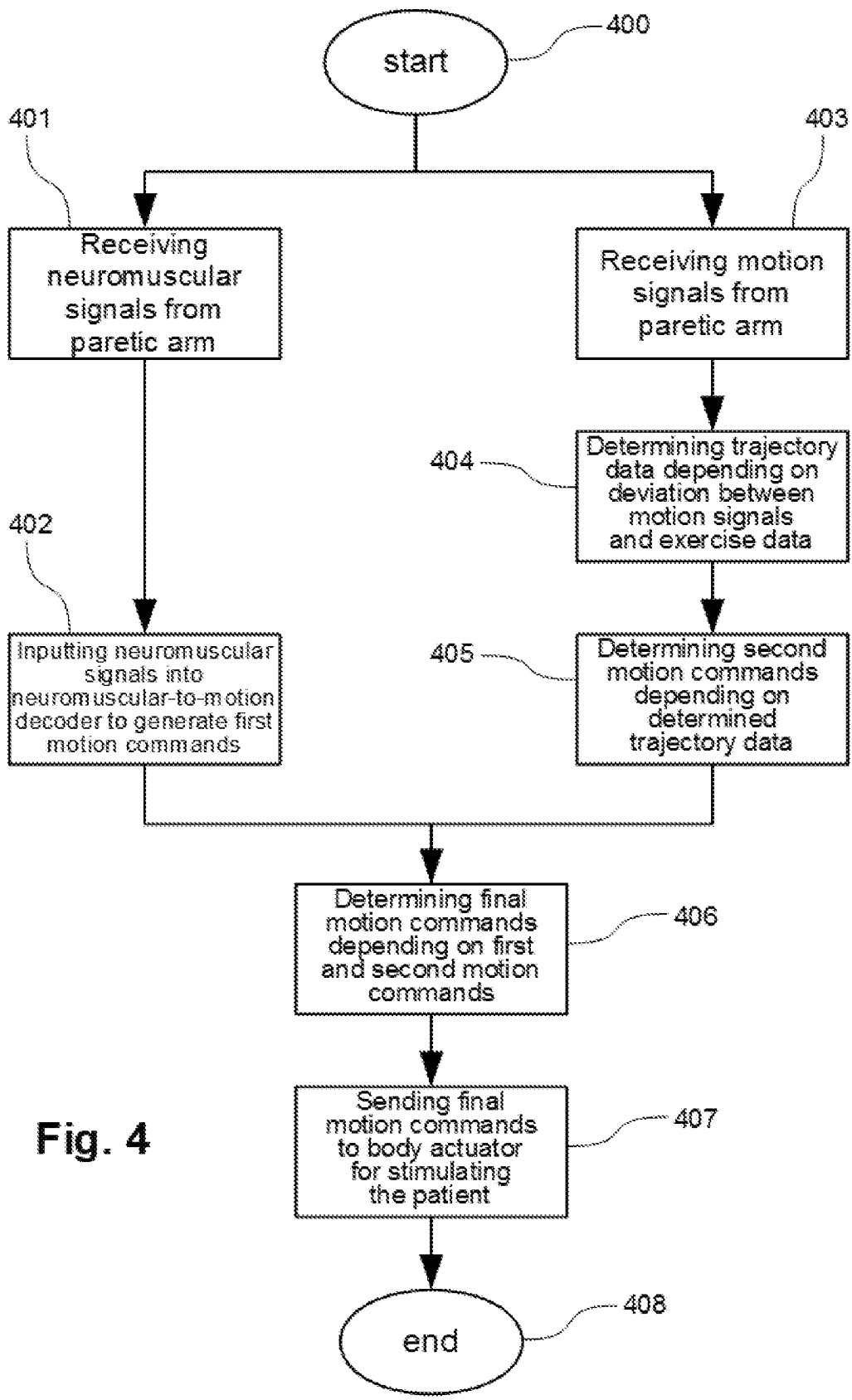
FIG. 4 is a flow chart schematically illustrating a rehabilitation method according to examples.

FIG. 4 is a flow chart schematically illustrating a rehabilitation method for rehabilitating a paretic arm (or leg) of a patient. This rehabilitation method may use the neuromuscular-to-motion decoder(s) generated by a generator method such as the one described with reference to FIG. 3.

This rehabilitation method may take into account (neuromuscular and motion) signals from the paretic arm of the patient during an attempt by the patient of performing the predefined exercise with the paretic arm.

This rehabilitation method may be performed by using a rehabilitation system similar to the ones described before with reference to previous figures. A computer program implementing the rehabilitation method may be stored and performed by the computer system 109. References to previous figures may also be included along the following description of FIG. 4.

At block 400, the rehabilitation method may be started when desired by an operator of the rehabilitation system.

The rehabilitation method may hence be triggered upon reception of a corresponding request inputted by the operator, for example.

At block 401, neuromuscular signals may be received (by the computer system 109) from neuromuscular sensors 101-104 attached to the paretic arm, during performance of the predefined exercise.

The attachment of the neuromuscular sensors 101-104 may be such that the neuromuscular sensors are associated to predefined muscle and/or nerve locations of the paretic arm (or leg) corresponding to predefined muscle and/or nerve locations of the healthy arm (or leg) taken into account in the generation of the neuromuscular-to-motion decoder to be used.

The rehabilitation system may provide audio and/or visual instructions to the patient of how to perform the predefined exercise.

At block 402, the neuromuscular signals may be inputted to the neuromuscular-to-motion decoder generated by corresponding generator method, for causing the neuromuscular-to-motion decoder to output first motion commands in different degrees of freedom (in exoskeleton-based examples) or permitted motion directions (in examples based on stimulation e.g. FES) under consideration.

The first motion commands may be seen as inductors of a motion due to the neuromuscular activity of the paretic arm, according to a cause-effect relationship between neuromuscular activity (cause) and motion (effect) of corresponding healthy arm, previously determined in the generator method.

At initial rehabilitation stages, said first motion commands may probably define a certainly erratic motion of the arm, so that a reduced weight may be initially attributed to the first motion commands.

At block 403, motion signals may be received from motion sensors (of the rehabilitation system) associated to predefined positions of the paretic arm (or leg) corresponding to predefined positions of the healthy arm (or leg) taken into account in the generation of the neuromuscular-to-motion decoder.

These motion signals may represent the motion that the paretic arm is actually following in the different degrees of freedom (or permitted motion directions) under consideration. The motion actually followed by the paretic arm may not match the trajectory to be followed as defined by the predefined exercise data.

At block 404, trajectory data defining a trajectory to be followed by the paretic arm may be determined depending on a deviation between the motion signals and the predefined exercise data, in the different degrees of freedom (or permitted motion directions) under consideration.

The determined trajectory data may be seen as defining a corrected trajectory of the motion actually followed by the paretic arm (according to the received motion signals) for redirecting the motion of the arm towards a valid trajectory (according to the predefined exercise data).

In final rehabilitation phases, the trajectory defined by the received motion signals and the trajectory defined by the predefined exercise data may substantially coincide, in which case no redirection of the motion of the arm may be considered.

At block 405, second motion commands may be determined depending on the determined trajectory data to be followed by the paretic limb, in the different degrees of freedom (or permitted motion directions) under consideration.

The second motion commands may be seen as inductors of a corrective motion for redirecting (if needed) the paretic arm towards a valid trajectory according to the predefined exercise data.

In some examples, a Linear-quadratic regulator (LQR) method may be used for determining the trajectory data at block 404, and for determining the second motion commands at block 405.

At block 406, final motion commands may be determined depending on the first motion commands (from block 402) and the second motion commands (from block 405), in the different degrees of freedom (or permitted motion directions) under consideration.

The final motion commands may thus be seen as a combination of inductors of motion due to the neuromuscular activity of the paretic arm (first motion commands) and inductors of motion to redirect (if required) the paretic arm towards a valid trajectory (second motion commands).

At block 407, the final motion commands may be sent to the body actuator (robotic exoskeleton and/or stimulation system e.g. FES) so as to suitably stimulate (or induce) the patient to perform the predefined exercise with the paretic arm (or leg).

The execution of the final motion commands by the body actuator may provoke a visual and proprioceptive feedback about the correctness of muscle/nerve activations of the patient. The body actuator induces a "hybrid" motion on the paretic arm combining an incorrect motion component due to incorrect neuromuscular activity, and a corrective motion component aimed at redirecting the arm towards a valid trajectory (for completing the predefined exercise successfully). At final rehabilitation stages, the neuromuscular activity in the paretic arm may be correct or minimally incorrect, in which case the corrective component may be substantially negligible.

Blocks 401-407 may be continuously performed until the predefined exercise with the paretic arm has been completed. In this case, the rehabilitation method proceeds to final block 408.

The determination of the final motion commands depending on the first motion commands and the second motion commands, in the different degrees of freedom (or permitted motion directions) under consideration, may be performed in a diversity of manners.

Figure 5:
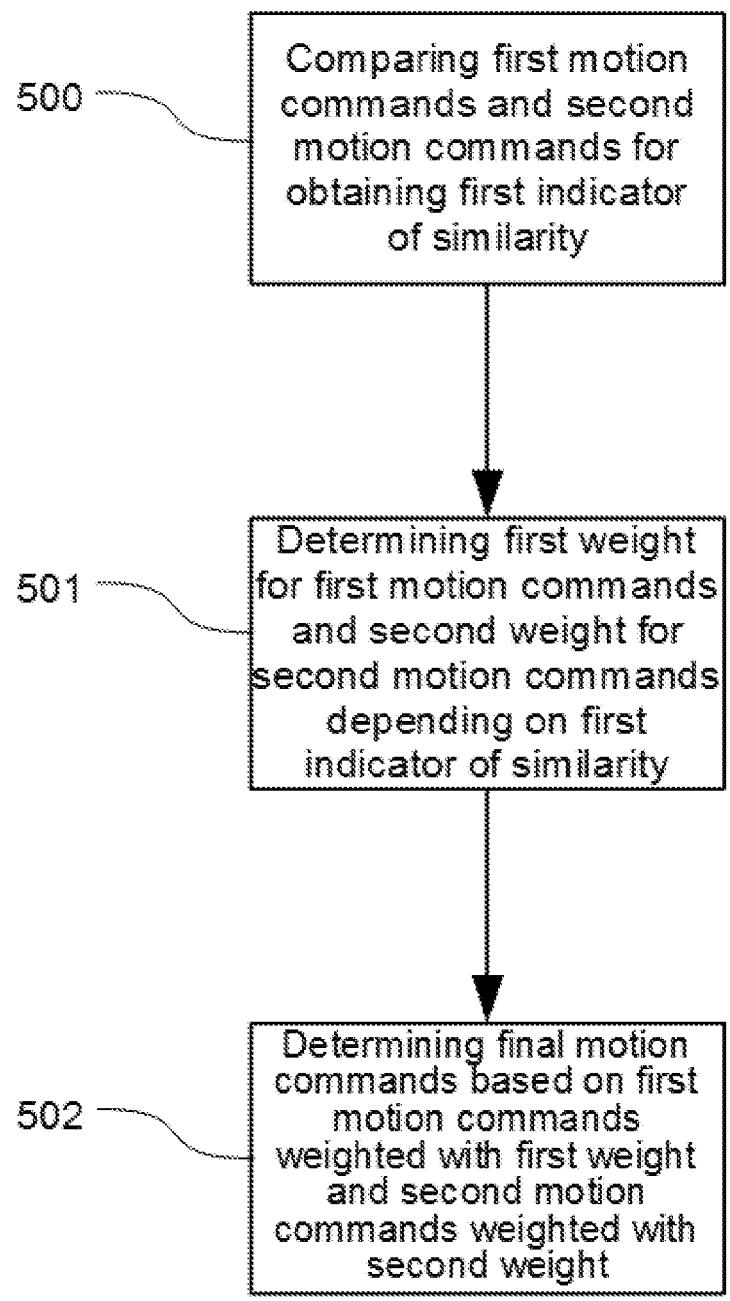
FIGS. 5-7 are flow charts schematically illustrating various examples of determining the final motion commands depending on first and second motion commands, in the context of a rehabilitation method similar to the one shown in FIG. 4.

FIG. 5 is a flow chart that schematically illustrates an example of determining the final motion commands depending on the first and second motion commands, in the context of a rehabilitation method similar to the one described with reference to FIG. 4.

At block 500, the first motion commands and the second motion commands may be compared for obtaining a first indicator of similarity, in each or some of the degrees of freedom (or permitted motion directions) under consideration. This comparison may be performed, in some examples, using a normalized root-mean-square error (NRMSE) method and/or a correlation coefficient method.

In alternative examples, the indicator of similarity may be determined (with similar results) by comparing the neuromuscular signals (from paretic limb) and the neuromuscular signals (from healthy limb) taken into account to generate the neuromuscular-to-motion decoder. In this case, for example, the computing system 109 may store the neuromuscular signals from healthy limb, along with the neuromuscular-to-motion decoder.

At block 501, a first weight may be determined for the first motion commands and a second weight may be determined for the second motion commands depending on the first indicator of similarity (obtained at previous block 500).

The determination of the first weight and the second weight may be such that the higher is the first indicator of similarity, the higher is the first weight and the lower is the second weight. In particular examples, the second weight may be determined as a function of the first weight.

At block 502, the final motion commands may be determined based on the first motion commands weighted with the first weight and the second motion commands weighted with the second weight.

For example, the final motion commands may be determined according to the following formula:

$$V_{final}=V_{neuro}*w_1+V_{assist}*w_2=V_{neuro}*w_1+V_{assist}*(1-w_1) \quad \text{Formula 1}$$

wherein $V_{final}$ is a final motion (e.g. velocity) command, $V_{neuro}$ is a first motion command (due to neuromuscular activity), $w_1$ is a first weight, $V_{assist}$ is a second motion command (for redirecting to valid trajectory) and $w_2$ is a second weight.

The first weight $w_1$ may be a value between 0 and 1, and the second weight $w_2$ may be equal to $1-w_1$ (as indicated in second part of Formula 1). This way, $w_1=0$ implies that $w_2=1$ and $V_{final}=V_{assist}$ which means that a completely assistive motion is induced by the body actuator on the arm (neuromuscular activity is ignored). Accordingly, $w_1=1$ implies that $w_2=0$ and $V_{final}=V_{neuro}$ which means that a motion fully depending on neuromuscular activity is induced by the body actuator on the arm (assistive component is ignored).

The more similar are the first motion commands $V_{neuro}$ (neuromuscular activity) to the second motion commands $V_{assist}$ (assistive control) the better may be considered the neuromuscular activity generated by the patient on the paretic arm. So, in this case, the final motion commands $V_{final}$ may be calculated with higher influence of $V_{neuro}$ (higher $w_1$) and lower influence of $V_{assist}$ (lower $w_2$).

The algorithm according to FIG. 5 and, in particular, to Formula 1 may be applied for each or some of the different degrees of freedom (or permitted motion directions) under consideration.

Figure 6:
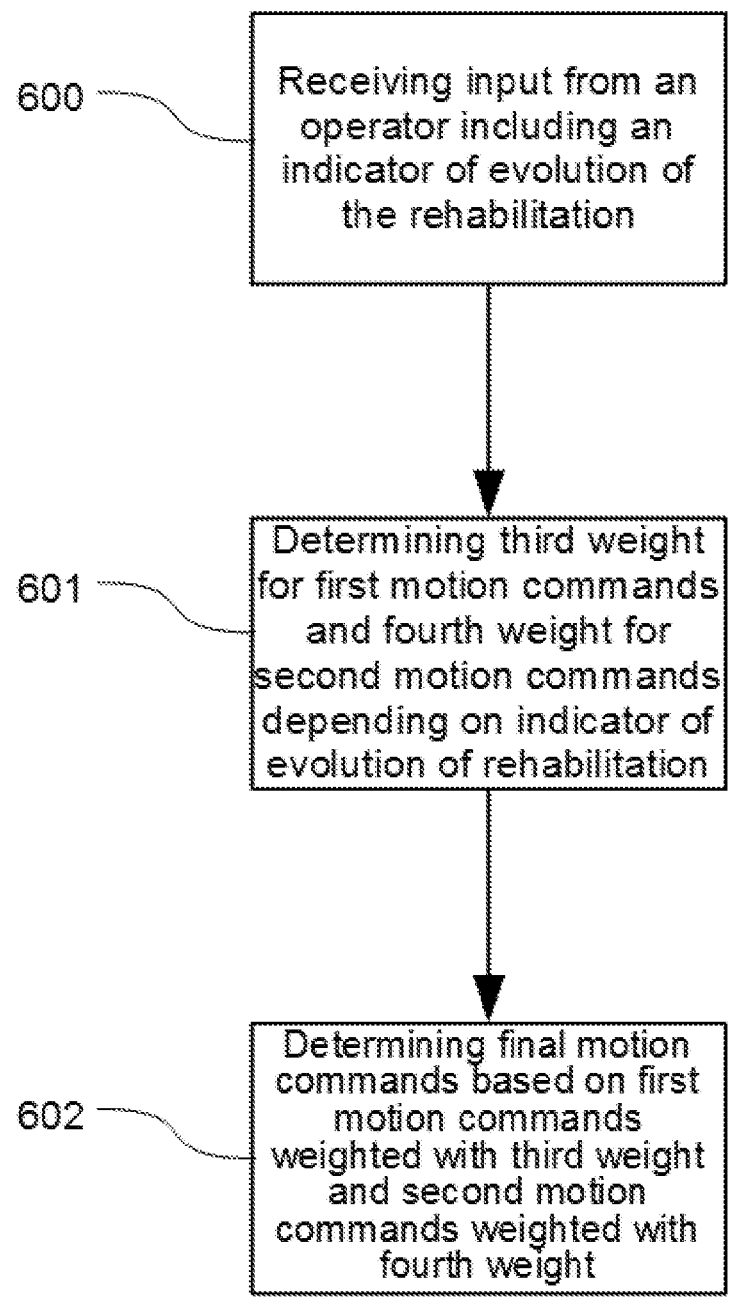

FIG. 6 is a flow chart that schematically illustrates a further example of determining the final motion commands depending on the first and second motion commands.

At block 600, input from a user, such as e.g. an operator of the rehabilitation system, may be received including an indicator of evolution of the rehabilitation of the patient. This indicator may be predetermined from previous executions of the rehabilitation method, for example.

At block 601, a third weight may be determined for the first motion commands and a fourth weight may be determined for the second motion commands, depending on the indicator of evolution of the rehabilitation (received at block 600).

The determination of the third weight and the fourth weight may be such that the higher is the indicator of evolution of the rehabilitation, the higher is the third weight and the lower is the fourth weight. In particular examples, the third weight may be determined as a function of the fourth weight.

At block 602, the final motion commands may be determined based on the first motion commands weighted with the third weight and the second motion commands weighted with the fourth weight.

For example, the final motion commands may be determined according to the following formula:

$$V_{final}=V_{neuro}*w_3+V_{assist}*w_4=V_{neuro}*w_3+V_{assist}*(1-w_3) \quad \text{Formula 2}$$

wherein $V_{final}$ is a final motion (e.g. velocity) command, $V_{neuro}$ is a first motion command (due to neuromuscular activity), $w_3$ is a third weight, $V_{assist}$ is a second motion command (for redirecting to valid trajectory) and $w_4$ is a fourth weight.

The higher is the indicator of evolution of the rehabilitation the better may be considered the evolution and, hence, the neuromuscular activity generated by the patient on the paretic arm. So, in this case, the final motion commands $V_{final}$ may be calculated with higher influence of $V_{neuro}$ (higher $w_3$) and lower influence of $V_{assist}$ (lower $w_4$). Weights $w_3$ and $w_4$ may be accordingly varied for that aim in a similar manner as described for weights $w_1$ and $w_2$ with respect to FIG. 5 and Formula 1.

The algorithm according to FIG. 6 and, in particular, to Formula 2 may be applied for each or some of the different degrees of freedom (or permitted motion directions) under consideration.

Figure 7:
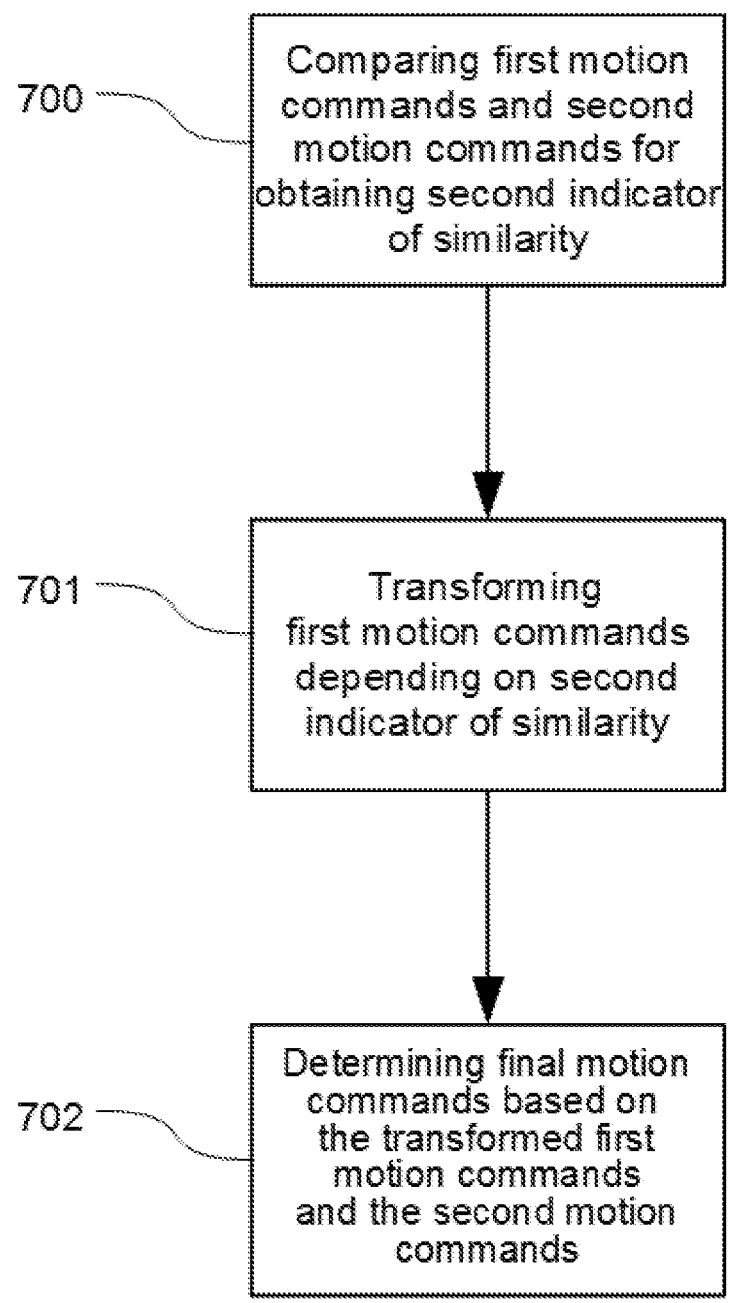

FIG. 7 is a flow chart that schematically illustrates a still further example of determining the final motion commands depending on the first and second motion commands.

At block 700, the first motion commands and the second motion commands may be compared for obtaining a second indicator of similarity between the first motion commands and the second motion commands, in each or some of the degrees of freedom (or permitted motion directions) under consideration.

At block 701, the first motion commands may be transformed based on the second indicator of similarity (between the first motion commands and the second motion commands). The first motion commands may be transformed based on a projection of vectors representing first motion commands on vectors representing second motion commands, for example. The first and second motion commands may be e.g. velocity vectors.

At block 702, the final motion commands may be determined based on the transformed first motion commands and the second motion commands.

For example, the final motion commands may be determined according to the following formula:

$$V_{final}=\text{transformed}(V_{neuro})+V_{assist} \quad \text{Formula 3}$$

wherein $V_{final}$ is a final motion (e.g. velocity) command, $V_{neuro}$ is a first motion command (due to neuromuscular activity), $V_{assist}$ is a second motion command (for redirecting to valid trajectory) and transformed($V_{neuro}$) is the transformed first motion command.

The algorithm according to FIG. 7 and, in particular, to Formula 3 may be applied for each or some of the different degrees of freedom (or permitted motion directions) under consideration.

In any of the described examples based on weights, said weights may be updated in real-time (within same rehabilitation session or same execution of rehabilitation method). Alternatively, said weights may be kept fixed during one or more rehabilitation sessions or executions of rehabilitation method.

In any of the described examples relating to generator and rehabilitation methods, the received neuromuscular signals may be (optionally) rectified, and (optionally) filtered, and (optionally) processed by an algorithm of features extraction, and (optionally) normalized, and (optionally) processed by an algorithm of dimensionality reduction. Examples of algorithms of dimensionality reduction are Principal Component Analysis (PCA), Independent Component Analysis (ICA), Non-negative matrix factorization (NMF), etc. Examples of features that can be extracted from neuromuscular signals are time-domain features, frequency-domain features, muscle synergies, etc.

With respect to the normalization of the neuromuscular signals, it is aimed at adjusting the neuromuscular signals irrespective of any difference in amplitude between neuromuscular signals from healthy limb and neuromuscular signals from paretic limb. The normalization may be performed using e.g. a Z-score method or any other method aimed at the mentioned purpose.

According to the Z-score method, the normalization may be carried out by applying the following formula:

$$\text{Normalized\_Neuro} = (\text{Neuro} - \text{mean})/\text{std} \qquad \text{Formula 4}$$

wherein Neuro is a neuromuscular signal to be normalized, Normalized_Neuro is the neuromuscular signal once normalized, mean is a mean of neuromuscular signals from same muscle/nerve location as Neuro, and std is a standard deviation of neuromuscular signals from same muscle/nerve location as Neuro.

Given a neuromuscular signal to be normalized, the mean and the standard deviation applicable to said signal may be calculated from neuromuscular signals previously received within the execution of the generator method or rehabilitation method.

In the case of generator method, the whole neuromuscular signals may be received (from healthy limb) and recorded in a first step and, subsequently, their normalization may be performed in a second step once the first step has been completed. This way, the mean and standard deviation to be used in the normalization may be calculated taking into account the whole neuromuscular signals (from healthy limb).

In the case of rehabilitation method, a predefined time interval of neuromuscular signals already received (from paretic limb) may be considered to calculate the mean and standard deviation. For example, the predefined time interval may comprise the last 60 seconds of already received neuromuscular signals.

Although only a number of examples have been disclosed herein, other alternatives, modifications, uses and/or equivalents thereof are possible. Furthermore, all possible combinations of the described examples are also covered.

The following clauses disclose in an unlimited way additional embodiments.

Clause 1. A generator system for generating a neuromuscular-to-motion decoder from a healthy limb of a person, the generator system comprising neuromuscular sensors, motion sensors, and a controller system that is configured to receive neuromuscular signals obtained by the neuromuscular sensors associated to predefined muscle and/or nerve locations of at least one pair of agonist and antagonist muscles/nerves of the healthy limb, said neuromuscular signals being obtained during performance by the person of a predefined exercise with the healthy limb, said predefined exercise being defined by predefined exercise data;

receive motion signals obtained by the motion sensors associated to predefined positions of the healthy limb, said motion signals being obtained during performance by the person of the predefined exercise with the healthy limb; and generate the neuromuscular-to-motion decoder by mapping the neuromuscular signals to the motion signals over time using a mapping method whereby the neuromuscular-to-motion decoder is to be used for rehabilitating a paretic limb.

Clause 2. A generator system according to clause 1, wherein the neuromuscular sensors comprise one or more electromyography (EMG) sensors, and/or one or more electroneurography (ENG) sensors, and/or one or more ultrasound sensors, and/or one or more optical sensors.

Clause 3. A generator system according to any of clauses 1 or 2, wherein the neuromuscular sensors comprise one or more invasive sensors, and/or one or more non-invasive sensors.

Clause 4. A generator system according to any of clauses 1 to 3, wherein the motion sensors are configured to generate the motion signals as velocity signals, and/or position signals, and/or torque signals, and/or force signals, and/or acceleration signals.

Clause 5. A generator system according to any of clauses 1 to 4, wherein the mapping method comprises a machine learning method, or a statistical method, or a data mining method, or a combination of at least some of them.

Clause 6. A generator system according to clause 5, wherein the mapping method comprises a support vector machine method, or a neural network method, or a fuzzy logic method, or a linear regression method, or a non-linear regression method, or a Lasso regression method, or a ridge regression method, or a Kalman filter method, or a combination of at least some of them.

Clause 7. A generator system according to any of clauses 1 to 6, wherein the controller system is configured to determine reproducible data of the predefined exercise based on the predefined exercise data; and send said reproducible data to a reproducing device so as to provide the person with audio and/or visual indications about the predefined exercise to be performed.

Clause 8. A generator system according to any of clauses 1 to 7, comprising a body actuator.

Clause 9. A generator system according to clause 8, wherein the body actuator is a robotic exoskeleton configured to be mounted on the healthy limb.

Clause 10. A generator system according to clause 9, wherein the motion sensors are comprised in the robotic exoskeleton.

Clause 11. A generator system according to any of clauses 9 or 10, wherein the robotic exoskeleton is configured to guide the person in performing the predefined exercise with the healthy limb based on the predefined exercise data.

Clause 12. A rehabilitation system for rehabilitating a paretic limb of a patient by using a neuromuscular-to-motion decoder generated by a generator system according to any of clauses 1 to 11, the rehabilitation system comprising neuromuscular sensors, motion sensors, and a controller system that is configured to receive neuromuscular signals obtained by the neuromuscular sensors associated to predefined muscle and/or nerve locations of the paretic limb corresponding to predefined muscle and/or nerve locations of a healthy limb taken into account in the generation of the neuromuscular-to-motion decoder, the neuromuscular signals being obtained during an attempt by the patient to perform with the paretic limb a predefined exercise defined by predefined exercise data taken into account in the generation of the neuromuscular-to-motion decoder;

input the neuromuscular signals to the neuromuscular-to-motion decoder for causing the neuromuscular-to-motion decoder to output first motion commands;

receive motion signals obtained by the motion sensors associated to predefined positions of the paretic limb corresponding to predefined positions of the healthy limb taken into account in the generation of the neuromuscular-to-motion decoder, the motion signals being obtained during the attempt by the patient to perform the predefined exercise with the paretic limb;

determine trajectory data defining a trajectory to be followed by the paretic limb depending on a deviation between the motion signals and the predefined exercise data;

determine second motion commands depending on the determined trajectory data to be followed by the paretic limb;

determine final motion commands depending on the first motion commands and the second motion commands; and send the final motion commands to a body actuator associated to the paretic limb for controlling the body actuator so as to stimulate the patient to perform the predefined exercise with the paretic limb.

Clause 13. A rehabilitation system according to clause 12, wherein the controller system is configured to determine the final motion commands depending on the first motion commands and the second motion commands by weighting the first motion commands and the second motion commands based on a predefined weighting criterion; and determining the final motion commands based on the weighted first and second motion commands.

Clause 14. A rehabilitation system according to clause 13, wherein the controller system is configured to weight the first motion commands and the second motion commands based on the predefined weighting criterion by comparing the first motion commands to the second motion commands for obtaining a first indicator of similarity between the first motion commands and the second motion commands; and determining a first weight for the first motion commands and a second weight for the second motion commands depending on the first indicator of similarity, in such a way that the higher is the first indicator of similarity, the higher is the first weight and the lower is the second weight; and wherein the controller system is configured to determine the final motion commands based on the first motion commands weighted with the first weight and the second motion commands weighted with the second weight.

Clause 15. A rehabilitation system according to clause 14, wherein the controller system is configured to compare the first motion commands to the second motion commands by performing a normalized root-mean-square error (NRMSE) method and/or a correlation coefficient method.

Clause 16. A rehabilitation system according to any of clauses 14 or 15, wherein the controller system is configured to determine the second weight as a function of the first weight.

Clause 17. A rehabilitation system according to clause 13, wherein the controller system is configured to weight the first motion commands and the second motion commands based on the predefined weighting criterion by receiving input from a user including an indicator of evolution of the rehabilitation; and weighting the first motion commands and the second motion commands based on the indicator of evolution of the rehabilitation.

Clause 18. A rehabilitation system according to clause 17, wherein the controller system is configured to weight the first motion commands and the second motion commands based on the indicator of evolution of the rehabilitation by determining a third weight for the first motion commands and a fourth weight for the second motion commands depending on the indicator of evolution of the rehabilitation, in such a way that the higher is the indicator of evolution of the rehabilitation, the higher is the third weight and the lower is the fourth weight; and wherein the controller system is configured to determine the final motion commands based on the first motion commands weighted with the third weight and the second motion commands weighted with the fourth weight.

Clause 19. A rehabilitation system according to clause 18, wherein the controller system is configured to determine the third weight as a function of the fourth weight.

Clause 20. A rehabilitation system according to clause 12, wherein the controller system is configured to determine the final motion commands depending on the first motion commands and the second motion commands by aggregating the first motion commands and the second motion commands.

Clause 21. A rehabilitation system according to clause 12, wherein the controller system is configured to determine the final motion commands depending on the first motion commands and the second motion commands by comparing the first motion commands to the second motion commands for obtaining a second indicator of similarity between the first motion commands and the second motion commands;

transforming the first motion commands based on the second indicator of similarity between the first motion commands and the second motion commands; and determining the final motion commands based on the transformed first motion commands and the second motion commands.

Clause 22. A rehabilitation system according to clause 21, wherein the controller system is configured to transform the first motion commands based on a projection of the first motion commands on the second motion commands.

Clause 23. A rehabilitation system according to clause 13, wherein the controller system is configured to weight the first motion commands and the second motion commands based on the predefined weighting criterion by comparing the received neuromuscular signals to neuromuscular signals taken into account to generate the neuromuscular-to-motion decoder, for obtaining a third indicator of similarity between the received neuromuscular signals and the neuromuscular signals taken into account to generate the neuromuscular-to-motion decoder; and determining a fifth weight for the first motion commands and a sixth weight for the second motion commands depending on the third indicator of similarity, in such a way that the higher is the third indicator of similarity, the higher is the sixth weight and the lower is the fifth weight; and wherein the controller system is configured to determine the final motion commands based on the first motion commands weighted with the fifth weight and the second motion commands weighted with the sixth weight.

Clause 24. A rehabilitation system according to any of clauses 12 to 23, wherein the controller system is configured to determine reproducible data of the predefined exercise based on the predefined exercise data; and send said reproducible data to a reproducing device so as to provide the patient with audio and/or visual indications about the predefined exercise to be attempted.

Clause 25. A rehabilitation system according to any of clauses 12 to 24, wherein the controller system is configured to determine the trajectory data defining the trajectory to be followed by the paretic limb based on a Linear-quadratic regulator (LQR) method.

Clause 26. A rehabilitation system according to any of clauses 12 to 25, wherein the neuromuscular sensors comprise one or more electromyography (EMG) sensors, and/or one or more electroneurography (ENG) sensors, and/or one or more ultrasound sensors, and/or one or more optical sensors.

Clause 27. A rehabilitation system according to any of clauses 12 to 26, wherein the neuromuscular sensors comprise one or more invasive sensors, and/or one or more non-invasive sensors.

Clause 28. A rehabilitation system according to any of clauses 12 to 27, wherein the motion sensors are configured to generate the motion signals as velocity signals, and/or position signals, and/or torque signals, and/or force signals, and/or acceleration signals.

Clause 29. A rehabilitation system according to any of clauses 12 to 28, comprising the body actuator.

Clause 30. A rehabilitation system according to clause 29, wherein the body actuator comprises a robotic exoskeleton configured to be mounted on the paretic limb.

Clause 31. A rehabilitation system according to clause 30, wherein the motion sensors are comprised in the robotic exoskeleton.

Clause 32. A rehabilitation system according to any of clauses 29 to 31, wherein the body actuator comprises a Functional electrical stimulation (FES) system, and/or an ultrasound-based neuromuscular stimulation system and/or an optical-based neuromuscular stimulation system.

Clause 33. A rehabilitation system according to any of clauses 12 to 32, comprising the generator system.

Clause 34. A rehabilitation system according to clause 33, wherein the neuromuscular sensors of the rehabilitation system and the neuromuscular sensors of the generator system are the same neuromuscular sensors.

Clause 35. A rehabilitation system according to any of clauses 33 or 34, wherein the motion sensors of the rehabilitation system and the motion sensors of the generator system are the same motion sensors.

Clause 36. A generator method for generating a neuromuscular-to-motion decoder from a healthy limb of a person, the generator method comprising receiving neuromuscular signals obtained by neuromuscular sensors associated to predefined muscle and/or nerve locations of at least one pair of agonist and antagonist muscles/nerves of the healthy limb, said neuromuscular signals being obtained during performance by the person of a predefined exercise with the healthy limb, and said predefined exercise being defined by predefined exercise data;

receiving motion signals obtained by motion sensors associated to predefined positions of the healthy limb, said motion signals being obtained during performance by the person of the predefined exercise with the healthy limb; and generating the neuromuscular-to-motion decoder by mapping the neuromuscular signals to the motion signals over time using a mapping method whereby the neuromuscular-to-motion decoder is to be used for rehabilitating a paretic limb.

Clause 37. A rehabilitation method for rehabilitating a paretic limb of a patient by using a neuromuscular-to-motion decoder generated by a generator method according to clause 36, the rehabilitation method comprising receiving neuromuscular signals obtained by neuromuscular sensors associated to predefined muscle and/or nerve locations of the paretic limb corresponding to predefined muscle and/or nerve locations of a healthy limb taken into account in the generation of the neuromuscular-to-motion decoder, the neuromuscular signals being obtained during an attempt by the patient to perform with the paretic limb a predefined exercise defined by predefined exercise data taken into account in the generation of the neuromuscular-to-motion decoder;

inputting the neuromuscular signals to the neuromuscular-to-motion decoder for causing the neuromuscular-to-motion decoder to output first motion commands;

receiving motion signals obtained by motion sensors associated to predefined positions of the paretic limb corresponding to predefined positions of the healthy limb taken into account in the generation of the neuromuscular-to-motion decoder, the motion signals being obtained during the attempt by the patient to perform the predefined exercise with the paretic limb;

determining trajectory data defining a trajectory to be followed by the paretic limb depending on a deviation between the motion signals and the predefined exercise data;

determining second motion commands depending on the determined trajectory data to be followed by the paretic limb;

determining final motion commands depending on the first motion commands and the second motion commands; and sending the final motion commands to a body actuator associated to the paretic limb for controlling the body actuator so as to stimulate the patient to perform the predefined exercise with the paretic limb.

Clause 38. A rehabilitation method according to clause 37, comprising the generator method.

Clause 39. A computing system comprising a memory and a processor, embodying instructions stored in the memory and executable by the processor, the instructions comprising functionality to execute a generator method according to clause 36 for generating a neuromuscular-to-motion decoder from a healthy limb of a person.

Clause 40. A computer program product comprising program instructions for causing a computing system to perform a generator method according to clause 36 for generating a neuromuscular-to-motion decoder from a healthy limb of a person.

Clause 41. A computer program product according to clause 40, embodied on a storage medium.

Clause 42. A computer program product according to clause 40, carried on a carrier signal.

Clause 43. A computing system comprising a memory and a processor, embodying instructions stored in the memory and executable by the processor, the instructions comprising functionality to execute a rehabilitation method according to any of clauses 37 or 38 for rehabilitating a paretic limb of a patient.

Clause 44. Computer program product comprising program instructions for causing a computing system to perform a rehabilitation method according to any of clauses 37 or 38 for rehabilitating a paretic limb of a patient.

What is claimed is:

1. A method of treating a paretic limb of a patient, the method comprising:

obtaining a neuromuscular-to-motion decoder using a computing system that includes a memory, a processor, and instructions stored in the memory executable by the processor, the instructions comprising functionality to execute a mapping method that maps first neuromuscular signals to first motion signals during a person performing a predefined exercise with a healthy limb, the mapping of the first neuromuscular signals to the first motion signals is performed using a method selected from the group consisting of a machine learning method, a statistical method, a data mining method and any combination of the machine learning method, statistical method and data mining method, the first neuromuscular signals having been generated by at least first and second neuromuscular sensors situated at first predefined locations on or in agonist and antagonist muscles of the healthy limb of the person during the person performing the predefined exercise, the first motion signals having been generated by a first plurality of motion sensors situated at second predefined locations on the healthy limb during the person performing the predefined exercise;

respectively placing at least third and fourth neuromuscular sensors at third predefined locations on or in the agonist and antagonist muscles of a paretic limb of the patient, the agonist and antagonist muscles of the paretic limb corresponding to the agonist and antagonist muscles of the healthy limb, the third predefined locations corresponding to the first predefined locations, the third and fourth neuromuscular sensors configured to produce second neuromuscular signals upon the patient attempting to perform the predefined exercise with the paretic limb;

inputting the second neuromuscular signals to the neuromuscular-to-motion decoder for causing the neuromuscular-to-motion decoder to output first motion commands;

placing a second plurality of motion sensors at fourth predefined locations on the paretic limb, the fourth predefined locations on the paretic limb corresponding to the second predefined locations of the healthy limb, the second plurality of motion sensors configured to produce second motion signals upon the patient attempting to perform the predefined exercise with the paretic limb;

producing trajectory data defining a trajectory to be followed by the paretic limb depending on a deviation between the second motion signals and predefined exercise data defining the predefined exercise;

producing second motion commands depending on the trajectory data to be followed by the paretic limb;

producing final motion commands depending on the first motion commands and the second motion commands; and sending the final motion commands to a body actuator associated to the paretic limb to cause the body actuator to stimulate the paretic limb to perform the predefined exercise, one or more of the first, second, third and fourth neuromuscular sensors being a sensor selected from the group consisting of an electromyography sensor, an electroneurography sensor, an ultrasound sensor, and an optical sensor, one or more of the first and second plurality of motion sensors being selected from the group consisting of an inertial sensor, a magnetic sensor, and an optical sensor.

2. The method of treating a paretic limb of a patient according to claim 1, wherein each of the at least third and fourth neuromuscular sensors and each of the at least first and second neuromuscular sensors are a same type of neuromuscular sensor.

3. The method of treating a paretic limb of a patient according to claim 1, wherein each of the second plurality of motion sensors and each of the first plurality of motion sensors are a same type of motion sensor.

4. The method of treating a paretic limb of a patient according to claim 1, wherein the final motion commands are produced depending on the first motion commands and the second motion commands by weighting the first motion commands and the second motion commands based on a predefined weighting criterion.

5. The method of treating a paretic limb of a patient according to claim 4, wherein the first motion commands and the second motion commands are weighted based on the predefined weighting criterion by:

comparing the first motion commands to the second motion commands to obtain a first indicator of similarity between the first motion commands and the second motion commands; and determining a first weight for the first motion commands and a second weight for the second motion commands depending on the first indicator of similarity, in such a way that the higher is the first indicator of similarity, the higher is the first weight and the lower is the second weight;

the final motion commands being produced based on the first motion commands weighted with the first weight and the second motion commands weighted with the second weight.

6. The method of treating a paretic limb of a patient according to claim 5, wherein the first motion commands and second motion commands are compared by performing a normalized root-mean-square error method and/or a correlation coefficient method.

7. The method of treating a paretic limb of a patient according to claim 4, wherein the first motion commands and the second motion commands are weighted based on the predefined weighting criterion by:

receiving input from a user that includes an indicator of evolution of the rehabilitation; and weighting the first motion commands and the second motion commands based on the indicator of evolution of the rehabilitation.

8. The method of treating a paretic limb of a patient according to claim 7, wherein the first motion commands and the second motion commands are weighted based on the indicator of evolution of the rehabilitation by determining a third weight for the first motion commands and a fourth weight for the second motion commands depending on the indicator of evolution of the rehabilitation, in such a way that the higher is the indicator of evolution of the rehabilitation, the higher is the third weight and the lower is the fourth weight;

the final motion commands being produced based on the first motion commands weighted with the third weight and the second motion commands weighted with the fourth weight.

9. The method of treating a paretic limb of a patient according to claim 1, wherein the final motion commands are produced depending on the first motion commands and the second motion commands either by:

aggregating the first motion commands and the second motion commands, or by comparing the first motion commands to the second motion commands to obtain a second indicator of similarity between the first motion commands and the second motion commands;

transforming the first motion commands based on the second indicator of similarity between the first motion commands and the second motion commands; and determining the final motion commands based on the transformed first motion commands and the second motion commands.

10. The method of treating a paretic limb of a patient according to claim 9, wherein the first motion commands are transformed based on a projection of the first motion commands on the second motion commands.

11. The method of treating a paretic limb of a patient according to claim 4, wherein the first motion commands and the second motion commands are weighted based on the predefined weighting criterion by:

comparing the second neuromuscular signals to the first neuromuscular signals for obtaining a third indicator of similarity between the second neuromuscular signals and the first neuromuscular signals; and determining a fifth weight for the first motion commands and a sixth weight for the second motion commands depending on the third indicator of similarity, in such a way that the higher is the third indicator of similarity, the higher is the sixth weight and the lower is the fifth weight;

the final motion commands being produced based on the first motion commands weighted with the fifth weight and the second motion commands weighted with the sixth weight.

12. The method of treating a paretic limb of a patient according to claim 1, wherein the trajectory data is produced based on a Linear-quadratic regulator method.

13. The method of treating a paretic limb of a patient according to claim 1, comprising fitting a robotic exoskeleton that includes the second plurality of motion sensors to the paretic limb.

14. The method of treating a paretic limb of a patient according to claim 1, comprising fitting a robotic exoskeleton that includes a Functional electrical stimulation system and/or an ultrasound-based neuromuscular stimulation system and/or an optical-based neuromuscular stimulation system.

15. The method of treating a paretic limb of a patient according to claim 1, wherein the person is the patient.

16. A system for treating a paretic limb of a person, the system comprising:

at least first and second neuromuscular sensors that are respectively configured for placement at first predefined locations on or in agonist and antagonist muscles of a healthy limb of a person, the first and second neuromuscular sensors configured to produce first neuromuscular signals upon the person performing a predefined exercise with the healthy limb;

a first plurality of motion sensors that are configured for placement at second predefined locations on the healthy limb, the first plurality of motion sensors configured to produce first motion signals upon the person performing the predefined exercise with the healthy limb;

at least third and fourth neuromuscular sensors that are respectively configured for placement at third predefined locations on or in agonist and antagonist muscles of a paretic limb of the person, the agonist and antagonist muscles of the paretic limb corresponding to the agonist and antagonist muscles of the healthy limb, the third predefined locations corresponding to the first predefined locations, the third and fourth neuromuscular sensors configured to produce second neuromuscular signals upon the person attempting to perform the predefined exercise with the paretic limb;

a second plurality of motion sensors that are configured for placement at fourth predefined locations on the paretic limb, the fourth predefined locations on the paretic limb corresponding to the second predefined locations of the healthy limb, the second plurality of motion sensors configured to produce second motion signals upon the person attempting to perform the predefined exercise with the paretic limb;

a body actuator associated with the paretic limb that is configured to stimulate the paretic limb to perform the predetermined exercise; and a control system comprising one or more memories and one or more hardware processors, wherein the one or more memories comprise instructions, that when executed by the one or more hardware processors, are operable to:

generate a neuromuscular-to-motion decoder by mapping the first neuromuscular signals to the first motion signals over time using a mapping method during the person performing the predefined exercise with the healthy limb, the mapping method selected from the group consisting of a machine learning method, a statistical method, a data mining method and any combination of the machine learning method, statistical method and data mining method;

input the second neuromuscular signals to the neuromuscular-to-motion decoder for causing the neuromuscular-to-motion decoder to output first motion commands;

produce trajectory data defining a trajectory to be followed by the paretic limb depending on a deviation between the second motion signals and predefined exercise data defining the predefined exercise;

produce second motion commands depending on the trajectory data to be followed by the paretic limb;

produce final motion commands depending on the first motion commands and the second motion commands; and send the final motion commands to the body actuator associated to the paretic limb to cause the body actuator to stimulate the paretic limb to perform the predefined exercise, one or more of the first, second, third and fourth neuromuscular sensors being a sensor selected from the group consisting of an electromyography sensor, an electroneurography sensor, an ultrasound sensor, and an optical sensor, one or more of the first and second plurality of motion sensors being selected from the group consisting of an inertial sensor, a magnetic sensor, and an optical sensor.

* * * * *